United States Patent
Kopinga

(10) Patent No.: US 11,819,587 B2
(45) Date of Patent: Nov. 21, 2023

(54) MONITORING OF STEAM QUALITY DURING STERILIZATION

(71) Applicant: SolidToo B.V., Veldhoven (NL)

(72) Inventor: Klaas Kopinga, Veldhoven (NL)

(73) Assignee: SolidToo B.V., Veldhoven (NL)

( * ) Notice: Subject to any disclaimer, the term of this patent is extended or adjusted under 35 U.S.C. 154(b) by 837 days.

(21) Appl. No.: 16/613,449

(22) PCT Filed: May 15, 2018

(86) PCT No.: PCT/EP2018/062577
§ 371 (c)(1),
(2) Date: Nov. 14, 2019

(87) PCT Pub. No.: WO2018/210850
PCT Pub. Date: Nov. 22, 2018

(65) Prior Publication Data
US 2021/0154346 A1    May 27, 2021

(30) Foreign Application Priority Data
May 17, 2017 (NL) ..................................... 2018932

(51) Int. Cl.
*G01N 33/00* (2006.01)
*A61L 2/26* (2006.01)
(Continued)

(52) U.S. Cl.
CPC .................. *A61L 2/26* (2013.01); *A61L 2/07* (2013.01); *G01N 25/00* (2013.01);
(Continued)

(58) Field of Classification Search
CPC ...................................................... G01N 25/00
See application file for complete search history.

(56) References Cited

U.S. PATENT DOCUMENTS 3,939,406 A * 2/1976 Billeter ..................... G01F 1/34
                                                                    324/636
6,464,938 B1   10/2002 Rongier

FOREIGN PATENT DOCUMENTS

DE         102010016017         11/2011
EP             1172117 A2 *      1/2002    ............... A61L 2/24
(Continued)

OTHER PUBLICATIONS

Van Doornmalen J P C M et aL: Measuring non-condensable gases in steam, Review of Scientific Instruments, Aip, Melville, NY, US, vol. 84, No. 11, Nov. 15, 2013.

*Primary Examiner* — Kevin Joyner
*Assistant Examiner* — Changru Chen
(74) *Attorney, Agent, or Firm* — N.V. Nederlandsch Octrooibureau

(57) ABSTRACT

An apparatus for measuring the steam quality is presented. The apparatus comprises a tube (1) with an open end (5) and a closed end. The open end has a fluid connection with the sterilizer chamber. At the closed end a heat sink (6) with a thermometer (7) is connected of which the temperature can be controlled. In the axial direction along the tube several thermometers (8) are attached to monitor the temperature profile along the tube. Apart from or instead of this, the device may comprise a thermal resistance (11) between the closed end of the tube and the heat sink. At different axial positions on this thermal resistance thermometers (10) may be attached to monitor the cooling power required to keep the heat sink at a predetermined temperature. Both the temperature profile and the cooling power are directly related to the fraction of non-condensable gases present in the sterilizer chamber.

17 Claims, 5 Drawing Sheets

(51) Int. Cl.
*A61L 2/07* (2006.01)
*G01N 25/00* (2006.01)

(52) U.S. Cl.
CPC ..... *G01N 33/0011* (2013.01); *G01N 33/0027* (2013.01); *A61L 2202/122* (2013.01); *A61L 2202/14* (2013.01)

(56) References Cited

FOREIGN PATENT DOCUMENTS

| EP | 1230936 A1 | * | 8/2002 | ............... A61L 2/28 |
| EP | 1674864 B1 | * | 9/2016 | ........... G01N 31/005 |
| WO | WO-2005056061 A1 | * | 6/2005 | ............... A61L 2/28 |
| WO | WO-2014046998 A1 | * | 3/2014 | ............... A61L 2/07 |

* cited by examiner

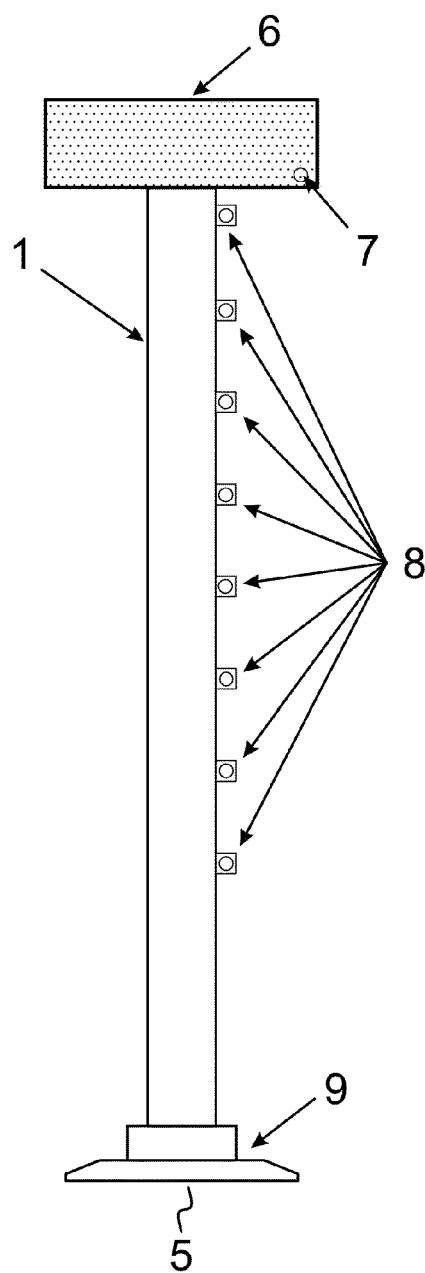
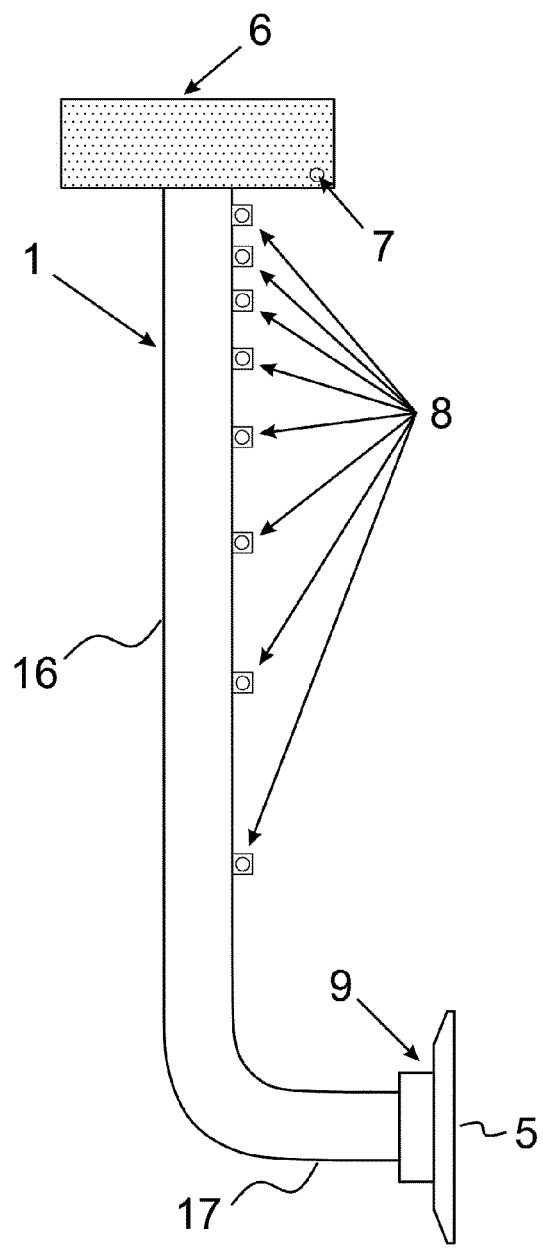
*FIG. 2A*    *FIG. 2B*

MONITORING OF STEAM QUALITY DURING STERILIZATION

FIELD OF THE INVENTION

The invention relates to a device and a method for detecting a gas in a fluid mixture. The invention in particular relates to detecting a non-condensable fluid in a gas mixture. The invention further relates to a device and a method to test and monitor steam quality during steam sterilization.

BACKGROUND OF THE INVENTION

Conditions for surface steam sterilization are predetermined time-temperature relations when saturated steam is present, e.g., 3 minutes at 134° C. with saturated steam [MRC59]. These surface steam sterilization conditions are derived from sterilization of aqueous liquids, in which the mechanism for the killing of organisms is coagulation of proteins [SYK67]. Sterilization is achieved if the liquid is kept at a certain elevated temperature for a sufficient amount of time. In the literature several temperature-time combinations for sterilization have been documented. The results for aqueous liquids can be used for surface steam sterilization [MRC59] if the steam heats up all surfaces to be sterilized to the required temperature and forms condensate on these surfaces. In the standard EN285 [EN285] this has been translated to the requirement that steam should have direct contact with the surfaces and the supplied steam may contain only a very small amount of non-condensable gases (NCGs) (3.5 vol. %, relative to the condensate, which corresponds to approximately 0.006 vol. % in the vapor phase). With NCGs in the steam gases are meant that will not condense in the pressure and temperature range of steam sterilization. These ranges are generally 0 to 350 kPa and 0 to 150° C., respectively. The NCGs can be introduced by or originate from the environmental air or dissolved gases in the feed water for the steam generation. Examples of NCGs originating from the environment are a bad air removal before the sterilization phase, leaks in the sterilizer or the connected devices, such as a vacuum pump, and compressed air injected into the sterilizer by leaks in valves controlled by compressed air (typically 700 kPa) and gaskets.

Steam sterilizers can contain various components, e.g., mechanical, electronical and software components. These components can malfunction unexpectedly. Also fluctuations in a steam supply can occur, for example, fluctuations in the amount of NCGs in the feed water for steam generation. It is known that steam quality (the amount of NCGs present in the steam) and the capacity for steam penetration of a sterilizer vary over the day [VDO16-3]. The importance of ensuring a correct steam sterilization process is acknowledged in the standards for steam sterilization [EN285, EN13060, ISO17665], patents [U.S. Pat. No. 5,270,217] and the literature [VDO13-2]. This demonstrates that monitoring is 'good practice' for steam sterilization processes. Moreover, according to these standards it is mandatory to monitor each load, e.g., ISO 17665 clause 10.1 specifies: 'Routine monitoring and control shall be performed on each operating cycle.' Currently, monitoring in steam sterilization is based on Biological, Chemical and Physical indicators.

Clause 8.2.4 of the standard EN 285 [EN285] specifies an air detector. This device is based on a tube that is connected to the steam sterilizer chamber at one end whereas the other end, outside of the steam sterilizer, is closed. The temperature at the closed end of the tube is measured with a temperature sensor. This air detector has only limited value, as already demonstrated in the note of clause 13.3.1 [EN285]: 'NOTE: This method does not necessarily express the true content of NCG in steam. The limiting value was defined experimentally in the 1960s in relation to the sensitivity of air detectors commonly used in the UK at that time. Repeated measurements give an idea of the true picture of NCGs in the steam supply.' Furthermore, because it qualifies conditions based on temperature measurements only, it cannot qualify steam concentration or the presence of air (NCGs). Finally, it is a channel with one end closed, of which the initial conditions are not specified and therefore not known. Therefore it is unclear what actually will be measured and where the energy for the observed temperature increase is coming from.

Biological monitoring is performed with biological indicators (BIs). These indicators have the disadvantage that their integrity can only be guaranteed if the storage and handling is performed according to the specifications given by the manufacturer. Apart from this, the incubation of the indicator will inevitably take time. Consequently, release of loads after sterilization will be delayed until the results of the indicators are available. Apart from this, their disadvantage is that they only provide a one sided test. This implies that in case of a problem, the information will often be insufficient for trouble shooting.

Chemical monitoring is performed with chemical indicators (CIs). Like the BIs, also these indicators only provide a one-sided test. One of the drawbacks of a CI is that it is rather inaccurate [VDO12-2] and many CIs have to be judged by subjective color interpretation [U.S. Pat. No. 4,115,068]. Additionally, the CI can only be interpreted after the complete sterilization cycle has been performed and the CI is taken out of the load. Also the CI is often intended to mimic a biological killing mechanism. The correspondence of the relatively simple chemical reactions with the complex biological killing mechanism is not obvious.

Currently, physical monitoring is mostly performed by monitoring pressure and temperature. From the pressure the so-called 'theoretical temperature' is calculated [EN285]. In the known method, the theoretical temperature is compared to the measured temperature. If the difference is less than 2 K the steam is accepted as saturated steam. However, according to the literature [IAWPS] this assumption is not correct. The calculation of the theoretical temperature is based on the pressure-temperature relation for saturated steam and, consequently, only valid when saturated steam is present. Only measuring pressure and temperature is not sufficient to ensure sterilization conditions [VDO14-1].

In some cases it is tried to measure if the steam injected into the steam sterilizer chamber is saturated. If that is the case the pressure-temperature relation for saturated steam is used again. However, even if this method would be accurate enough, insufficiently removed initial air and leaks in the sterilizer chamber will not be detected. Consequently, steam sterilization conditions cannot be ensured by measuring the steam quality in the supply line of steam (outside of the sterilizer chamber), as is done by, e.g., the 'SteamSpy' from MMM GmbH, Germany [DE102010016017A1].

Over the years, a variety of physical instruments have been developed with the aim to detect the presence of NCGs in the steam which is present in the sterilizer chamber. Many of these comprise a tube that is located outside the sterilizer chamber, often connected to the drain of the sterilizer. This tube is closed at one end and designed such that the steam in the tube condenses and the NCGs are entrapped. The volume of the entrapped NCGs is assumed to be a measure of the fraction of NCGs present in the sterilizer chamber. In some cases the presence of NCGs in the tube is deduced from temperature measurements [U.S. Pat. Nos. 3,402,991, 3,479,131], in other cases the volume of the entrapped air is measured quantitatively, e.g., by measuring the water displacement [U.S. Pat. No. 3,967,494] or by optical means [EP0841069A2]. A fundamental limitation of these methods is that the length of the tube used in these instruments is often so large, that the volume of the collected NCGs significantly lags behind the concentration of NCGs present in the sterilizer chamber. Therefore these techniques are not suited to monitor the steam quality in real time. Apart from this, it is not clear to which extent these instruments yield quantitative information about the fraction of NCG's in the sterilizer chamber itself.

Finally, physical or electronic test systems that intend to measure the steam quality within the sterilizer chamber are available in the market. It is reported that 3 out of 4 commercially available tests do not fulfil the claimed standard [BEN11]. DE202006006926U1 discloses a device called EBI 15 (Ebro Electronic GmbH, Ingolstadt, Germany). EP1230936A1 discloses a device called DPCD-3, Digital Process Challenge Device version 3 professional (Interster International BV, Wormerveer, the Netherlands). One device is based on the time derivative of the temperature [VDO13-3]. This is the 3M™ Electronic Test System (ETS), 3M Deutschland GmbH, Neuss, Germany [WO201047139]. It is based on the difference in heat transfer of steam and NCGs [VDO13-3]. This device should only be used as a steam penetration test as specified in the ISO 11140 part 4 [ISO11140-4]. This device is designed to use it only once a day. The results of the test are only available after the sterilization process has finished, which makes the instrument unsuitable to monitor the steam quality in real time. Finally, like all biological and chemical monitoring products mentioned so far, it requires manual handling of human operators of sterilizers. This costs time in a production environment and has the risk of human errors. U.S. Pat. No. 4,594,223 discloses heat sinks to identify NCGs.

SUMMARY OF THE INVENTION

It would be advantageous to be able to detect a particular gas in a gas mixture. More particularly it would be advantageous to be able to detect presence of non-condensable gases in a fluid containing multiple components, such as steam.

According to an aspect of the invention, a device is provided to measure the steam quality during the sterilization process, wherein an output signal of the device can be quantitatively related to the amount of NCGs in the sterilizer chamber.

According to an aspect of the invention, a device for detecting a gas, for example a non-condensable fluid in a gas mixture, comprises
  a tube having an open end and a closed end, wherein the tube and the closed end are closed with respect to a fluid, and the open end is open to allow the fluid to move into and out of the tube; and
  a heat sink configured to extract heat from the tube at the closed end of the tube.

The open end of the tube allows a fluid mixture to move into and out of the tube, among others by diffusion. A gas mixture that is present at the open end of the tube will thus enter into the tube. By extracting heat from the tube at the closed end of the tube, a temperature gradient occurs in the axial direction along the tube. That is, the heat sink causes the temperature at the closed end of the tube to be lower than the temperature at the open end of the tube. Condensable components of the gas mixture may thus condense inside the tube due to the lower temperature near the closed end of the tube. The condensed portion of the fluid may be removed from the tube by gravitation, while leaving any non-condensable gases inside the tube. The non-condensable gases may be forced towards the closed end of the tube by e.g. an inflow of the gas mixture that takes the place of the condensed fluid. The conditions thus created inside the tube may be measured in any suitable way, in order to detect the non-condensable gases near the closed end of the tube. This way information about the composition of the fluid that enters the tube through the open end of the tube may be obtained.

The heat sink may comprise a cooling surface that is fixed facing the device. This is a suitable configuration to extract heat from the tube specifically at the closed end of the tube. For example, the cooling surface faces the closed end of the tube.

The heat sink may be configured to cool at least the closed end of the tube down to a temperature below a condensation temperature of water. This way, the water component of the fluid condenses, leaving any non-condensable fluid in gaseous phase inside the tube.

The heat sink may comprise an active cooling element, for example a Peltier element. This allows to adjust the cooling power. Also it allows the continuous use of the device by actively keeping the cooling element cool during operation.

The device may comprise at least one thermometer configured to measure a temperature at a specific portion of the device or the fluid inside the tube. This allows to perform certain control and analysis functions, such as controlling the cooling power and/or analyzing the contents of the tube.

The device may comprise a control unit configured to adjust a cooling power of the heat sink based on a temperature obtained from the thermometer. In a particular example, the control unit may be configured to adjust the cooling power of the heat sink to maintain a predetermined fixed target temperature at the closed end of the tube.

The control unit may be configured to determine information about a composition of the fluid inside the tube, in particular about a presence of any non-condensable gas in the fluid, based on a temperature obtained from the thermometer or a cooling power of the heat sink. This is particularly advantageous, because it provides a cost effective and reliable way to detect non-condensable gases. This information may be generated in real time, so that any changes in gas composition may be acted on immediately.

The device may comprise a plurality of thermometers arranged along the tube in an axial direction of the tube, each thermometer of the plurality of thermometers being configured to measure a temperature at a different portion of the tube. This provides detailed information of the temperature along the tube, which was found to be strongly correlated to the presence of non-condensable gases. Thus, the control unit may be configured to analyze a temperature profile along the tube in axial direction obtained from the plurality of thermometers.

A distance between adjacent thermometers measured in axial direction along the tube may be larger for thermometers that are further away from the closed end of the tube in comparison to thermometers that are closer to the closed end of the tube. This is advantageous because the temperature gradient may be stronger near the cooled closed end of the tube.

The device may be configured to measure a flow of heat between the closed end of the tube and the heat sink. The amount of heat that flows from the closed end of the tube to the heat sink was found to be a suitable alternative quantity that is correlated to the composition of the fluid and the presence of non-condensable gases in particular. Thus the control unit can use this information to determine the composition.

The device may comprise a thermal resistor disposed in between the closed end of the tube and the heat sink; and a first thermometer configured to measure a first temperature of the thermal resistor and a second thermometer configured to measure a second temperature of the thermal resistor, wherein the first thermometer is fixed closer to the heat sink than the second thermometer, and the second thermometer is fixed closer to the closed end of the tube than the first thermometer. This is a suitable manner to measure the flow of heat between the closed end of the tube and the heat sink.

The device according may comprise a container, wherein the open end of the tube is fluidly connected to an inside of the container via an opening in a wall of the container, and wherein the container is closable to form a substantially closable chamber that is fluidly connected to a lumen of the tube. This way the tube is fluidly connected to the chamber, so that the device can detect the presence of non-condensable gases inside the chamber.

The chamber formed by the container may be a sterilizer chamber. This is an important application of the device, since the presence of non-condensable gases needs to be detected in order to ensure successful sterilization.

The container may have an opening in a side wall or an upper wall of the container, wherein the chamber is fluidly connected to the inside of the tube via the opening. The opening in the upper wall or side wall of the container allows the condensed fluid to flow back into the chamber.

The tube may be fixed to the side wall or upper wall of the container and the tube may protrude from the container in an upward direction. This allows improved flowback of the condensed fluid back into the container.

A distance along a center of the tube from the open end to the closed end may be between 10 cm and 20 cm. A diameter of the lumen of the tube may be between 4 mm and 15 mm. A thickness of the wall of the tube may be between 1 mm and 3 mm. The tube may be made of a metal such as Cu, Al, Cr, Fe, or Ni, or any alloy containing any two or more of these elements, or a polymer. These dimensions and material properties were found to work for the detection of non-condensable gases, in particular in conjunction with sterilizer chambers. However, this is not a limitation. Other dimensions and materials may be used, depending on the application at hand.

According to another aspect of the invention, a method is provided to determine a composition of a fluid. The method comprises providing steam to a tube having an open end and a closed end, wherein the tube and the closed end are closed with respect to the steam, and the open end is open to allow the steam to move into and out of the tube; and extracting heat from the tube at the closed end of the tube using a heat sink.

The person skilled in the art will understand that the features described above may be combined in any way deemed useful. Moreover, modifications and variations described in respect of the system may likewise be applied to the method, and modifications and variations described in respect of the method may likewise be applied to the system.

BRIEF DESCRIPTION OF THE DRAWINGS

The present invention will be discussed in more detail below, with reference to the attached drawings. Throughout the drawings, similar items may be indicated by means of the same reference numerals. It is noted that the drawings are not on scale.

FIG. 2A illustrates an example of a measurement probe using the temperature distribution along the tube, which can be mounted to e.g. the upper wall of a sterilizer chamber.

FIG. 2B illustrates an example of a measurement probe using the temperature distribution along the tube, which can be mounted to e.g. a side wall of a sterilizer chamber.

DETAILED DESCRIPTION OF EMBODIMENTS

Figure 1A:
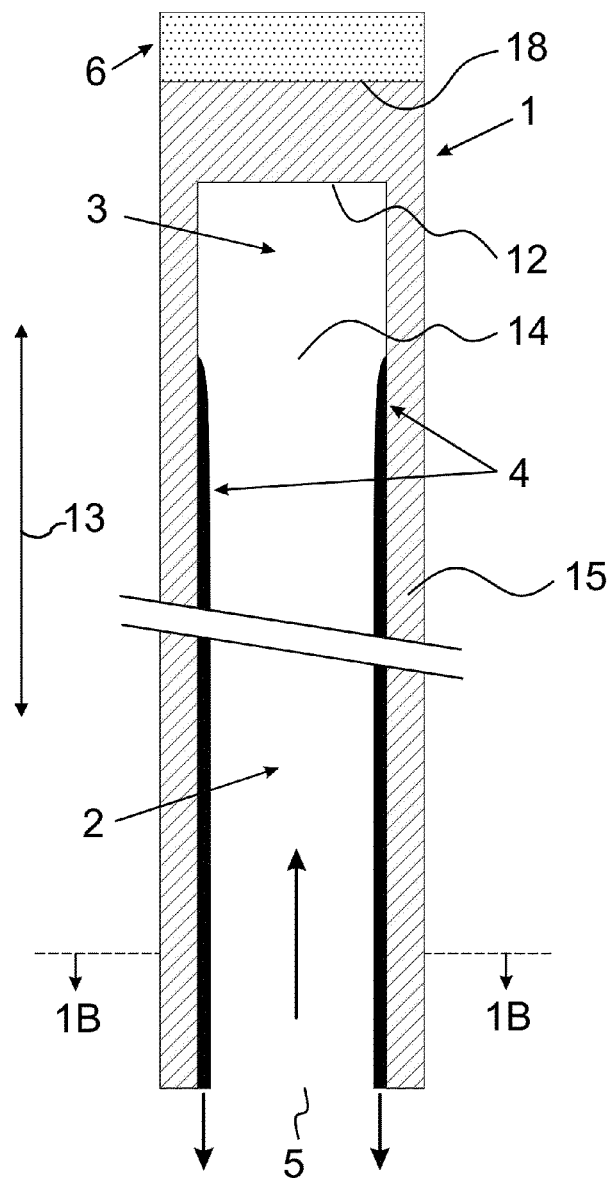
FIG. 1A shows a longitudinal cross section of a device to illustrate a principle of NCG detection using a tube in which condensation occurs.

Certain exemplary embodiments will be described in greater detail, with reference to the accompanying drawings.

The matters disclosed in the description, such as detailed construction and elements, are provided to assist in a comprehensive understanding of the exemplary embodiments. Accordingly, it is apparent that the exemplary embodiments can be carried out without those specifically defined matters. Also, well-known operations or structures are not described in detail herein, since they would obscure the description with unnecessary detail.

One approach to assess steam quality is to measure parameters that are very sensitive to the presence of small amounts of NCGs (generally air), such as the speed of condensation and the resulting heat transfer from steam to a surface.

According to an aspect of the present disclosure, an apparatus for measuring NCGs comprises a hollow tube, closed at one end, comprising a thermally conductive wall, thermometers to measure the temperature distribution along the tube in the axial direction, and a facility to control the temperature of the closed end of the tube. The temperature distribution along the tube provides information about the amount of NCGs present in the sterilizer chamber.

According to another aspect of the present disclosure, an apparatus for measuring NCGs comprises a hollow tube, closed at one end, comprising a thermally conductive wall, a thermometer to measure the temperature of the tube near the closed end of the tube, and a facility to control the temperature of the closed end of the tube. The power needed to cool the closed end of the tube to a fixed temperature provides information about the amount of NCGs present in the sterilizer chamber.

According to an aspect of the present disclosure, the apparatus may comprise a steam sterilizer comprising a sterilizer chamber, wherein the steam sterilizer is configured to inject steam into the sterilizer chamber to sterilize an object within the sterilizer chamber; wherein the open end of the tube has a fluid connection to the sterilizer chamber. The fluid connection of the tube to the sterilizer chamber allows assessing the steam conditions inside the sterilizer chamber. The steam sterilizer may further be configured to evacuate the sterilizer chamber before injecting the steam or to perform evacuation of sterilizer chamber and injection of the steam alternatingly.

According to another aspect of the present disclosure, the steam sterilizer may be configured to repeat the steps of evacuation and injection until the amount of NCGs detected by the apparatus satisfies a certain predetermined constraint.

The measurement tube may be connected to any wall of the sterilizer chamber but preferably not to the bottom wall. However, it is still possible to connect the tube to the bottom of a container such as a sterilizer chamber. In such a case, preferably a way to drain condensed liquid out of the tube is provided.

The apparatus may comprise a control unit configured to, repeatedly during a sterilization process performed by the steam sterilizer, receive the temperature distribution along the tube and/or the power needed to cool the closed end of the tube. This is helpful to assess during what time period or which time periods the sterilization conditions are met. For example, sterilization standards may prescribe a certain period of time during which saturated steam should be present at the surfaces that have to be sterilized. By analyzing the temperature distribution and/or the cooling power repeatedly during an interval, it can be assessed whether the prescribed period has been reached.

The steam sterilizer may be configured to adjust the sterilization process based on analysis of the temperature distribution along the tube and/or the cooling power of the cooling element. For example, if sufficient cooling power is needed at a given time period t, then the steam sterilizer may be configured to continue its sterilization process for at least a predetermined time interval $\Delta t$, up to $t+\Delta t$. Also, if too little cooling power is needed at a time at which saturated steam was expected to be present, the sterilizer may be configured to adjust the process for example by increasing the supply of steam. Other manners of adjusting the process based on the observed temperature distribution and/or cooling power may also be applied.

Figure 1B:
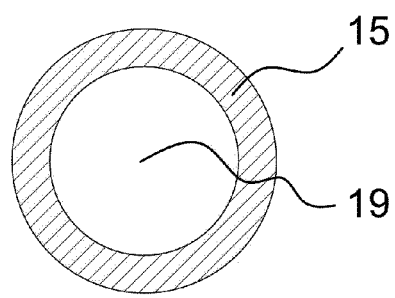
FIG. 1B shows an axial cross section of the device shown in FIG. 1A.

The approach described above may be implemented in various ways, of which an example is illustrated in FIG. 1. The illustrative device comprises a vertically oriented tube 1 with an open bottom end 5, which is fluidly connected to the sterilizer chamber, whereas the other end 12 is closed. Before the start of steam penetration in a process, the tube may have a temperature much lower than the sterilization temperature, for instance, room temperature. During the process, a mixture of steam and air 2 may enter the lumen 19 of the tube 1. As long as the wall of the tube has a lower temperature than the saturation temperature of the steam in the gas mixture entering the tube, the steam will condense on the wall of the tube. The condensate 4 runs off the wall towards the bottom of the tube, where it leaves the tube through the open end 5. If the wall of the tube is kept at a temperature below the saturation temperature of the steam, this condensation will establish a continuous flow of steam (and air) into the tube during the process until the end of the sterilization phase. Air flowing with the steam into the tube will not condense and can only leave the tube 1 via the open end 5 of the tube by diffusion. However, diffusion is a very slow process compared to the flow initiated by the condensing steam on the wall. Therefore, in the tube, air will accumulate and the concentration of water vapor will substantially decrease. This effect will be more pronounced towards the closed end 12 of the tube, where so much air 3 can be present that the steam will not be able to penetrate until the closed end 12.

The heat transfer from the gas mixture to the wall of the tube is dominated by the latent heat that is released during condensation of the steam. The presence of even small amounts of air will significantly reduce this heat transfer. Therefore, it is expected that the heat load on the tube close to the closed end 12 is smaller than the heat load on the tube close to the open end 5.

In the following, exemplary aspects of a device to analyze steam will be described in greater detail. However, it will be understood that the details disclosed herein are merely intended as illustrative examples. In certain implementations, the tube 1 is made of a material that has good heat conduction properties. Also, the heat conduction in axial direction may be good. For example, the heat conductivity of the tube material may be isotropic. The open end 5 of the tube may be connected to a side wall or upper wall of a sterilizer chamber, such that its entrance has a fluid connection to the sterilizer chamber 401. The closed end 12 of the tube may be kept at a constant temperature by a cooling facility 6. This cooling facility 6 may comprise a heat sink, cooled by environmental air, and/or a cooling liquid, but may also be implemented by other means, for instance, by using a Peltier cooler. The complete tube 1 may be thermally isolated from its environment, except for the cooling facility 6 and the open end 5 of the tube 1. The cooling of the closed end 12 of the tube 1, in combination with the heat conduction of the tube 1 in the axial direction 13, favors a wall temperature which is below the saturation temperature of the steam comprised in the steam-air mixture entering the lumen of the tube 1 through the open end 5 of the tube 1. The resulting dynamics of the steam-air mixture inside the lumen has already been outlined above. Using thermodynamic calculations, it can be shown that in the above-described configuration, the temperature distribution along the axial direction of the tube is directly related to the fraction of air that is present in the steam-air mixture at the entrance of the tube. Background information regarding thermodynamic computations has been reported in the literature [VDO13-3].

If the diameter of the tube is much smaller than its length, for example if the diameter of the tube is at least about a factor 10 smaller than its length, the transport of the steam-air mixture within the lumen 14 of the tube 1 can be described fairly accurately by a one-dimensional model. In such a model, the equation for the conservation of mass of a mixture component i (which may be, for example, steam or air) may be given by:

$$\frac{\partial \rho_i}{\partial t} + \frac{\partial \rho_i \bar{u}}{\partial t} = \frac{\partial}{\partial z}\left(\rho D^* \frac{\partial (\rho_i/\rho)}{\partial z}\right).$$

Herein, t is the time, $\rho_i$ the density of component i, $\rho$ the total density of the mixture, $\bar{u}$ the local velocity of the mixture averaged over the tube inner cross section, and z the (axial) position along the tube. $D^*$ is a modified diffusion constant, which appears because of the radial dependence of the velocity (Taylor dispersion). The boundary conditions at the open end 5 of the tube (z=0) are determined by the steam-air mixture in the sterilizer chamber.

The heat transfer from the steam-air mixture to the wall of the tube is dominated by the condensation of water vapor. This heat transfer can be described by standard Nusselt boundary layer theory. In very good approximation, the local heat transfer per meter ($q_m$) from saturated steam to the wall of the tube is given by:

$$q_m(z) = P_m(z)\{T_{sat}(z) - T_w(z)\}^{3/4}(z - L_{tube})^{-1/4}.$$

Here $T_{sat}$ is the saturation temperature of the steam, $T_w$ the wall temperature, $L_{tube}$ the tube length and $P_m$ a parameter with dimension W/m which depends on several physical properties of water and steam and the tube diameter. If non-condensable gases, such as air, are present, the heat transfer to the wall is significantly lower. This can be accounted for by making $P_m$ a function of the air fraction. More details about heat transfer can be found in the literature [VDO13-3].

If the outer side of the tube is thermally isolated from its environment, the temperature $T_w$ of the wall can be described by:

$$\frac{\partial T_w}{\partial t} = \frac{k_{w,z} A_{w,z}}{C_w} \frac{\partial^2 T_w}{\partial^2 z} + q_m.$$

Herein, $k_{w,z}$ denotes the heat conductivity of the tube wall in the axial direction 13 and $A_{w,z}$ denotes the cross-sectional area of the tube wall 15 perpendicular to the axial direction. $C_w$ represents the heat capacity of the tube wall 15 per meter in axial direction and $q_m$ denotes the heat transfer from the gas mixture to the tube wall by condensation.

Numerical solutions, for example, of the resulting set of three coupled second order partial differential equations may show the behavior that was qualitatively outlined above. At very low fractions of air in the sterilizer chamber, the steam penetrates almost towards the closed end 12 of the tube, resulting in a temperature of the part of the tube wall towards the open end 5 of the tube 1 that is almost equal to that of saturated steam, whereas the temperature of the tube wall drops to that of the heat sink near the closed end 12 of the tube 1. As the fraction of air in the sterilizer chamber increases, more air accumulates near the closed end 12 of the tube 1, and the temperature drop along the tube wall occurs at larger distance from the closed end 12, closer to the open end 5. Therefore, the temperature profile along the tube 1 in the axial direction 13 provides information about the fraction of air that is present in the sterilizer chamber 401. The numerical computations also reveal that the temperature distribution along the tube responds to changes in the air fraction within the sterilizer chamber rather quickly. For example, for a tube with a length of 15 cm, equilibrium may be established within a few seconds for small air fractions, increasing up to a few minutes for air fractions which are so large that they would preclude proper sterilization conditions within the sterilizer chamber. This implies that the device disclosed herein can provide information about the fraction of air within the sterilizer chamber at time scales that are generally much smaller than the time scale of a typical sterilization process. This is a large advantage compared to other instruments, such as the ETS, which have a more or less integrating behavior and/or yield results only after the complete sterilization process has finished.

FIG. 2A shows an example of a possible realization of a measurement device. The realization according to FIG. 2A is implemented using a straight tube. For example, the measurement device can be mounted vertically on the upper wall of a sterilizer chamber. The open end 5 may be fluidly connected to the interior of the sterilizer chamber. However, the device can be applied differently, to measure steam and gas properties in any kind of application besides sterilizer chambers.

FIG. 2B shows another example of a measurement device. The realization shown in FIG. 2B may be mounted, for instance, on a side wall of the sterilizer chamber, in such a way that the tube has a substantially vertically oriented portion 16 and a substantially horizontally oriented portion 17. However, this is not a limitation. In some other embodiments, the tube may be diagonally oriented, or curved, for example. In certain embodiments, the tube 1 is fixed to the sterilizer chamber in such a way that the condensed liquid on the inner wall of the tube 1 flows back towards the opening 5 and flows back out of the tube 1 back into e.g. the sterilizer chamber by gravity. In both realizations of FIG. 2A and FIG. 2B, the tube 1 may be connected to a flange 9 that allows the device to be easily connected to e.g. a sterilizer, but many alternative means to connect the device are possible instead of the flange 9. On the heat sink 6 a thermometer 7 may be attached that may be used to read and/or control the temperature of the heat sink 6. Along the tube 1, several thermometers 8 may be attached. These thermometers may serve to monitor the temperature profile in the axial direction 13 along the tube. In the device shown in FIG. 2A, the thermometers 8 are attached to the tube with equal spacing; in the device shown in FIG. 2B the spacing between adjacent thermometers becomes gradually smaller towards the closed end of the tube. The latter implementation may enhance the resolution of the instrument in case of relatively small air fractions in the sterilizer chamber, because for these fractions the steam penetrates further into the tube. The number of thermometers included in the figures and their spacing are only shown by means of example; many other configurations are possible. For example, the equal spacing shown in FIG. 2A may be applied to the curved tube shown in FIG. 2B, and the unequal spacing of the thermometers as shown in FIG. 2B may be applied to the straight tube shown in FIG. 2A.

When the temperature drop occurs near the closed end of the tube, the distance from the place of the temperature drop to the heat sink is small. This implies that a relatively large cooling power is consumed by the heat sink to keep the heat sink at the chosen temperature. If the temperature drop occurs at a larger distance from the heat sink, the cooling power is significantly smaller. Therefore, the cooling power needed to keep the heat sink at the chosen temperature is directly related to the position of the temperature drop along the tube and, consequently, to the fraction of non-condensable gas, such as air, in the sterilizer chamber. Thus, the control unit may be configured to detect the presence of non-condensable gases based on the cooling power needed to keep the closed end of the tube or the heat sink at the chosen temperature.

Figure 3A:
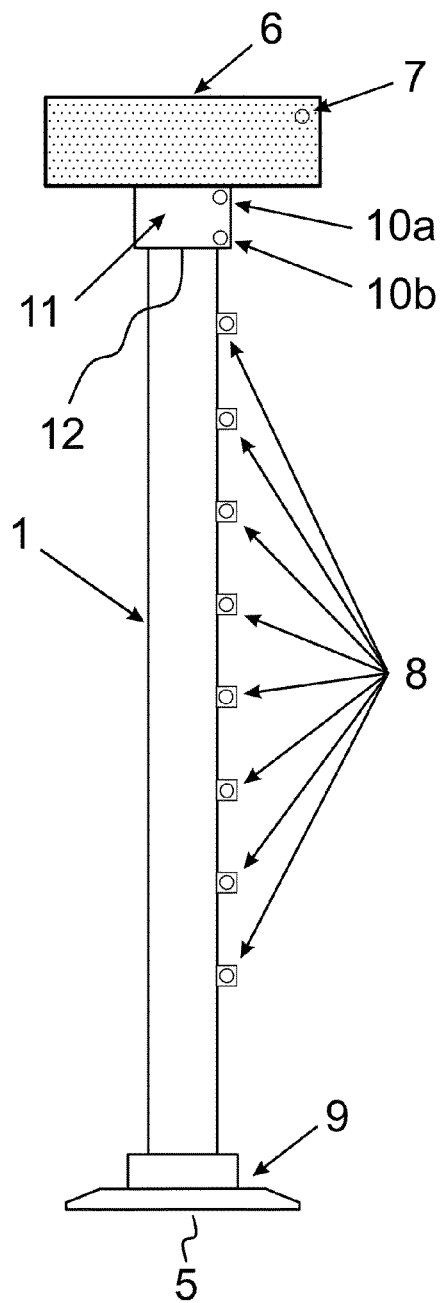
FIG. 3A illustrates an example of a measurement probe using the power needed to cool the closed end of the tube, which can be mounted to e.g. the upper wall of a sterilizer chamber.
Figure 3B:
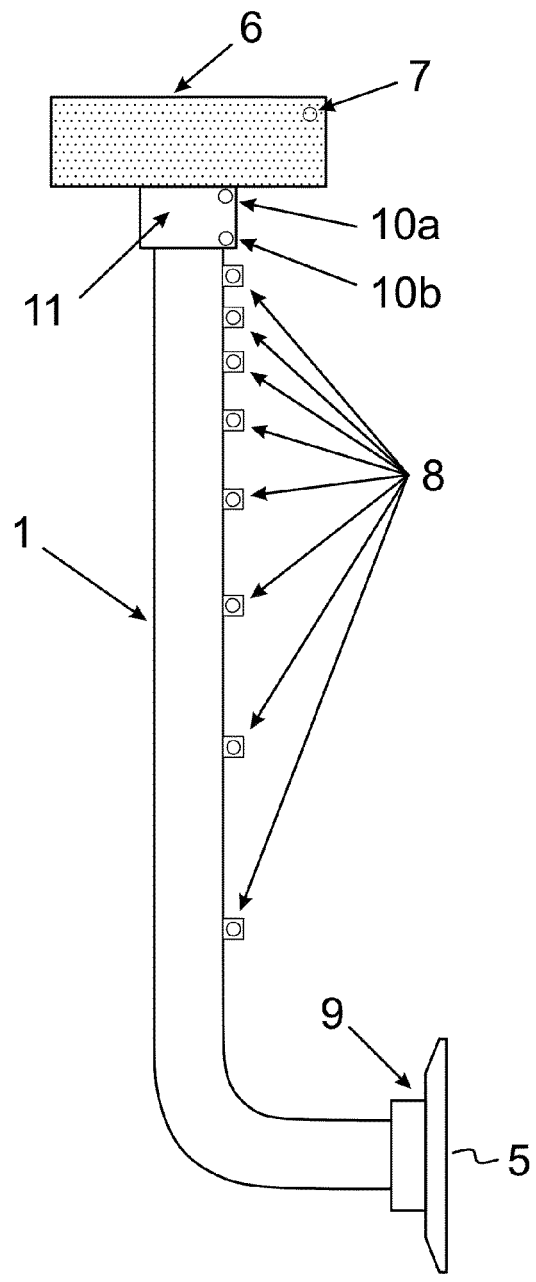
FIG. 3B illustrates an example of a measurement probe using the power needed to cool the closed end of the tube, which can be mounted to e.g. a side wall of a sterilizer chamber.

An example of a realization of a measurement device based on this principle is shown in FIG. 3A and FIG. 3B. In the examples of FIG. 3A and FIG. 3B the thermometers 8 along the tube 1 may be omitted, even though they have been illustrated in the drawing. A thermal resistance 11 has been disposed between the heat sink 6 and the closed end 12 of the tube 1. One thermometer 7 may be attached to the heat sink, to monitor and/or control the temperature of the heat sink 6. Two thermometers 10 may be attached to the thermal resistance 11 between the heat sink 6 and the closed end 12 of the tube 1. Of the two thermometers 10, a first thermometer 10a is fixed closer to the heat sink 6 than a second thermometer 10*b*, and the second thermometer 10*b* is fixed closer to the closed end 12 of the tube 1 than the first thermometer 10*a*.

At least two different ways are possible to determine the power consumed to cool the closed end 12 of the tube 1 to a chosen temperature. First, the power can be deduced from the externally supplied cooling power (either thermal or electronic), while keeping the temperature measured with the thermometer 7 at the chosen temperature. Second, this cooling power can alternatively be deduced from the temperature difference between the two thermometers 10 attached to the thermal resistance 11. It should be noted that if the cooling power is deduced from the externally supplied cooling power, only one of the thermometers illustrated at 7 and 10 (or even 8) are needed, and the remaining illustrated thermometers can be omitted. It should be noted that the realizations depicted in FIG. 3 are only examples; also combinations of the features depicted in FIG. 2 and FIG. 3 are possible.

FIG. 3A and FIG. 3B differ in the shape of the tube and the axial distribution of the thermometers 8 along the tube 1. These differences can be combined in any way as explained above with reference to FIG. 2A and FIG. 2B.

In a specific, more detailed, example of a possible realization of the device according to FIG. 2A and FIG. 2B the tube 1 may have a length of about 15 cm, an inner diameter (=lumen diameter) of about 6 mm, and an outer diameter of about 10 mm (thus, a thickness of the tube wall of about 2 mm). The tube may be made of, for example, a metal, such as stainless steel. For example, stainless steel grade 316L may be used. The open end 5 may be fitted with a flange 9, for example a Triclamp flange, to enable easy fixation to the sterilizer chamber. The flange 9 may be fitted to the sterilizer chamber in such a way that the lumen of the tube is in fluid communication with the inside of the sterilizer chamber via the open end 5 of the tube 1 and a hole in the wall of the sterilizer chamber. The thermometers 7, 8, 10 may comprise thermocouples, for example, type K thermocouples. In such a configuration the heat conduction in the axial direction 13 of the tube may be about $10^{-3}$ Wm/K. The heat sink 6 may be controlled to maintain a temperature of about 45° C. However, these numerical values are only provided as illustrative examples.

The dimensions and materials of the tube can be chosen with a great variability. As a practical example, a length measured along a central axis of the tube (1) from the open end (5) to the closed end (12) can be between 10 cm and 30 cm. A diameter of a cross section of the lumen of the tube (1) can be between 3 mm and 20 mm. Also, a thickness of the wall (15) of the tube (1) can be between 1 mm and 5 mm. As to the material, as examples, the tube may be made of thermally conductive materials such as a metal such as Cu, Al, Cr, Fe, or Ni, or any alloy containing any two or more of these elements. Alternatively, the tube may be made of a polymer. In any of the disclosed embodiments, the tube may be covered by a thermally isolating material. Also, in any of the disclosed embodiments, the heat sink at the closed end of the tube may be the only heat sink of the measurement device. That is, in certain embodiments, no further heat sinks are provided along the tube. In certain embodiments, during detection of non-condensable gases, no further active heat sinks are activated except for the heat sink at the closed end of the tube.

Condensation properties of a gas depend on the temperature and pressure that is applied to the gas. Accordingly, where in this disclosure "non-condensable gas" is mentioned, this may be understood to be a gas that does not condense at the applied temperature and pressure, i.e., a non-condensing gas.

During the sterilization phase of a sterilization process, the temperature profile along the tube may decrease almost linearly from the sterilization temperature (for instance, 134° C.) at the open end of the tube to the maintained temperature of the heat sink (for instance, 45° C.) at the closed end, when large fractions of air (for example, about 1%) are present in the sterilizer chamber. In such a situation, the power needed to cool the heat sink may be of the order of about 0.5 W, for example. For smaller air fractions (0.05%) during the sterilization phase, the temperature of the tube at 5 cm away from the closed end 12 may be as high as 134° C., and may decrease from 134° C. at 5 cm from the closed end of the tube to 45° C. at the closed end. In that case, the power needed to cool the heat sink may be larger, for example of the order of about 2 W. For very small air fractions (0.005%), the temperature may decrease from 134° C. at 2 cm from the closed end of the tube to 45° C. at the closed end during the sterilization phase. In that case, the power needed to cool the heat sink may be of the order of about 5 W. These numbers depend on the actual configuration (materials, dimensions, etc.) of the device.

A calibration procedure and/or numerical solutions of the equations disclosed above may be used to relate the temperature readings of the thermometers and/or the power needed to cool the heat sink to the chosen temperature to the air (NCG) fraction in the sterilizer chamber.

Figure 4:
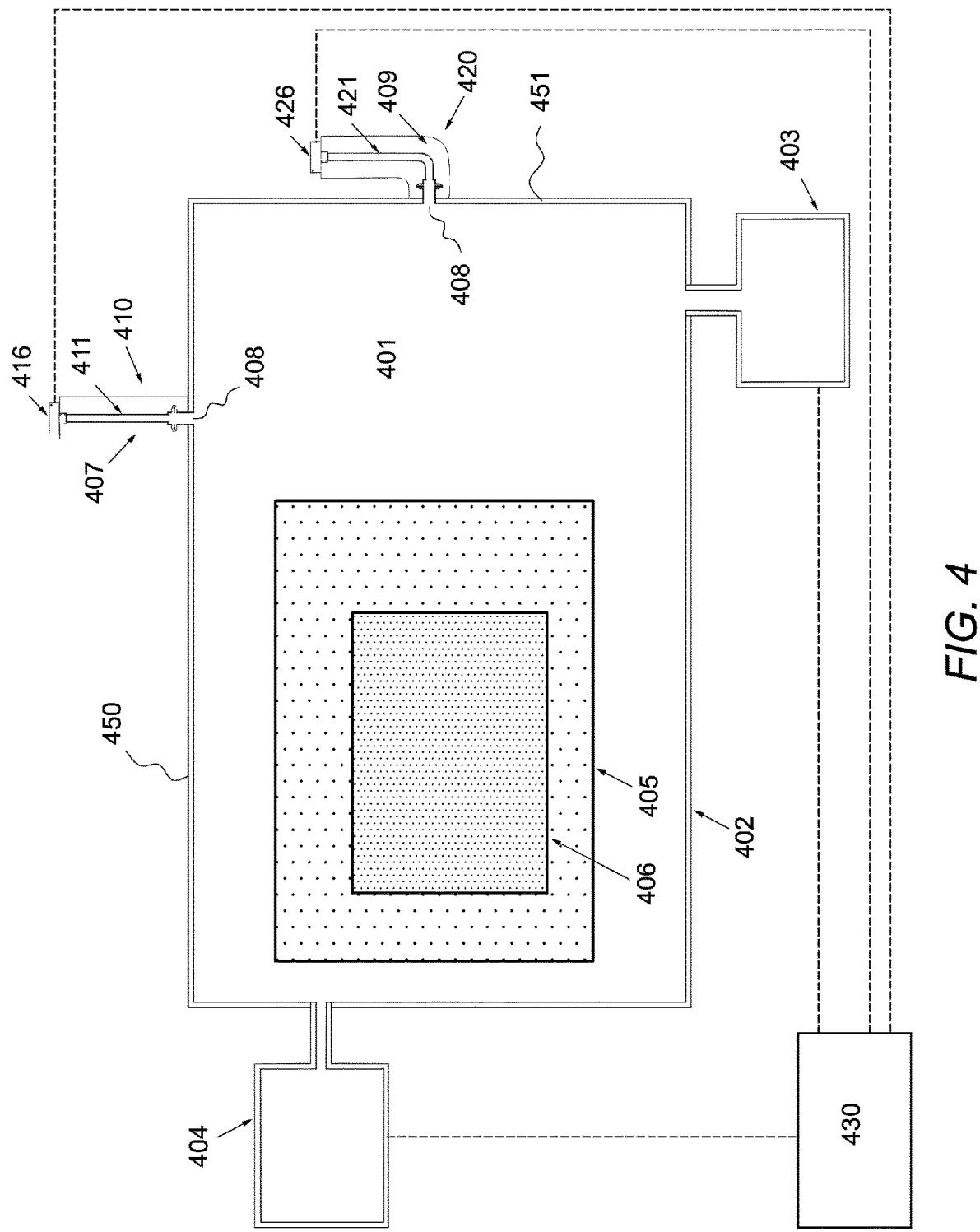
FIG. 4 illustrates some examples of locations of the measurement probes at the wall of a sterilizer chamber.

FIG. 4 shows a schematic representation of a sterilizer apparatus. Only features relevant to an understanding of the present disclosure have been illustrated in FIG. 4. Features not necessary for an understanding of the measurement device have been omitted. The sterilizer apparatus comprises walls 402 forming an at least substantially closable sterilizer chamber 401. The sterilizer chamber 401 may have a loadable space 405, in which load 406 may be put. For example, at least one of the walls 402 may comprise a closable opening for inserting and removing the load 406 into and out of the sterilizer chamber 401. This load 406 may comprise for example a pack of textile and/or one or more medical devices to be sterilized. Such medical devices may include heavy instruments and/or tubular instruments such as catheters, which warm up very slowly if substantial fractions of NCGs are present within the sterilizer chamber.

The sterilizer chamber 401 may be fluidly connected to a pump 403. When the sterilizer chamber 401 is closed, the pump 403 may be optionally be configured to perform a pumping operation to remove any fluid from the sterilizer chamber 401 to create a vacuum inside the sterilizer chamber 401. The sterilizer may also comprise a steam generator 404 including a water supply and facilities to vaporize and heat the water. The steam may be conditioned, so that steam that is injected into the sterilizer chamber 401 may have predetermined properties including for example a predetermined temperature and/or a predetermined humidity. The steam generator 404 may comprise an electrical or other type of heating element to heat and vaporize the water. Alternatively, the steam may be supplied from an external source, such as a central steam generator of a hospital.

A typical sterilization process comprises three phases. The first phase is the conditioning phase, during which the air that is initially present in the sterilizer chamber is removed and the load is heated up to the sterilization temperature. This is generally achieved by successive cycles of evacuating the chamber by the pump 401 and injecting saturated steam from the steam generator 404. The second phase is the actual sterilization phase, during which the sterilizer chamber is filled with saturated steam and kept at the specified temperature (generally by controlling the pressure) for a specified time. During the third phase the sterilizer chamber is evacuated to dry the load and finally filled with air to atmospheric pressure to return to a safe state where it can be opened. Notwithstanding the above-disclosed typical sterilization process, alternative processes may be used to achieve the steam sterilization. The measurement devices disclosed herein may be used in conjunction with any suitable sterilization process.

One or more measurement devices can be used to monitor the sterilizing conditions inside the sterilizer chamber 401. However, the measurement devices disclosed herein may also be used in other measurement applications. Moreover, the measurement devices disclosed herein are not limited to being used in conjunction with a sterilizer or sterilization procedures. Rather, they can be used to measure steam quality properties of any gas mixture, in particular steam. In an exemplary implementation, the gas mixture is in a container, and the device (in particular the open end of the tube) is in fluid communication with the gas mixture inside the container.

FIG. 4 illustrates two examples of how a measurement device according to the present disclosure may be arranged with respect to the sterilizer chamber 401. However, these arrangements are only disclosed by means of examples, without limiting the present disclosure thereto. As discussed above, the sterilizer chamber 401 could be replaced with any kind of container. The application of the measurement device to any kind of container may be realized in a similar way.

In the first example, the measurement device 410 is fitted to the upper wall 450 of the sterilizer chamber 401 such that the lumen of the tube 411 has a fluid connection to the interior of the sterilizer chamber 402. The tube 411 of the device 410 is thermally insulated from the environment by an insulating material 407. In this way, heat transport in the radial direction from the tube 411 of the device 410 to the environment is greatly reduced. A part of the heat sink 416 may be in thermal contact with the environment, either directly or indirectly, to enable control of the heat sink temperature (i.e., to transport heat away from the tube 411 towards the environment).

In the second example, the measurement device 420 is connected to a side wall 451 of the sterilizer chamber 401. The setup including tube 421, thermally insulating material 409, and heat sink 426 is otherwise similar to that outlined for the first example.

To promote that the condensed steam exits the tube by gravity and returns into the sterilizer chamber, the tube 411 of the measurement device 410 is a straight tube extending in vertical direction from the upper wall 450. Likewise, the tube 421 of the measurement device 420 extends from the side wall 451 of the sterilizer and tends in an upward direction.

In a practical implementation, typically either one of the devices 410 and 420 will be provided, and the other one omitted. However, this is not a limitation. It is also possible to provide more than one measurement device to provide multiple measurements of the same container.

In any of the above arrangements, the thermometers may be read out by a data-acquisition system, which processes and analyzes the temperature profile in the axial direction of the tube and/or the cooling power applied to keep the heat sink at the chosen temperature. This analysis may, for example, yield the fraction of air that is present in the steam-air mixture in the sterilizer chamber 401. The analysis may involve looking up the detected temperature(s) and/or cooling power in a look-up table and retrieving the fraction of air from the look-up table. The look-up table may be generated by suitable experiments and/or may be computed based on the above-disclosed equations.

The results of this analysis may be used, for example, to generate an alarm signal if the fraction of NCGs during the sterilization phase is above a predetermined threshold. On the other hand, the results can (also) be sent to a control unit 430, which may be configured to control the operation of the sterilizer chamber 401 including injection of steam by the steam generator 404 and removal of fluid from the sterilizer chamber by the pump 403. Also, the control unit 430 may be configured to receive the measurement signals and/or measurement data generated by the device 410 and/or the device 420. The control unit 430 may be configured to generate an alarm signal if the fraction of NCGs is determined to be above a predetermined threshold. The control unit 430 may also be configured to adapt dynamically, for instance, the timing of the sterilization process based on the measurement result and/or the alarm signal.

The control unit 430 may be configured to provide real-time information about the measured values and/or computed values. Also, the control unit 430 may be configured to detect the steam quality (the fraction of NCGs) during every sterilizing process.

Also, the control unit 430 may be configured to deliver at least some of the detected and/or computed results to an external system (not illustrated), such as a hospital 'track and trace' information system. In such a system, the digital information may be coupled to specific patient files. Also, the digital information can be coupled to a relevant instrument. This relevant instrument can be the sterilizer device. Alternatively, digital information can be coupled to the device that was sterilized. Also, the digital information can be coupled to a maintenance system associated with the sterilizer device. For example, if malfunctioning is detected, the system can send a signal to a maintenance service, so that service may be provided to repair the sterilizer device. Additionally, the information of the sterilization process used for medical devices can be coupled to patient files in order to improve patient safety.

The devices and methods disclosed herein allow monitoring variables that are relevant for determining steam sterilization conditions. They allow monitoring steam quality for every load of the sterilizer. The device can provide the measurement information in real-time. Also, it can be used to obtain more insight in the steam sterilization processes.

The system offers the possibility to monitor directly whether sterilization conditions are satisfied or not. The data of the measurements can be made available in real-time, so they can be used for process control or process optimization.

In an alternative implementation, the tube 1 of the device may be fixed or positioned loosely inside a space or container containing the fluid to be analyzed. Insulation material around the tube may be provided to still be able to create the temperature conditions as described hereinabove. If the heat sink 6 is a passive heat sink, such as a thermal capacitor, which may be made from aluminum, the insulating material may be provided around the heat sink as well. If the heat sink 6 comprises an active cooling element, for example a Peltier element, the insulation material may be omitted at a heat source of the cooling element, so that heat can be actively removed from the tube 1. The heat source of the cooling element may be attached to an opening in the wall of the container, so that the cooling element can operate more efficiently.

By appropriately tuning the temperatures, including the target temperature of the heat sink and the look-up tables correlating measurements with information regarding NCGs, the device can be used to detect non-condensable fluids in other gases.

Figure 5:
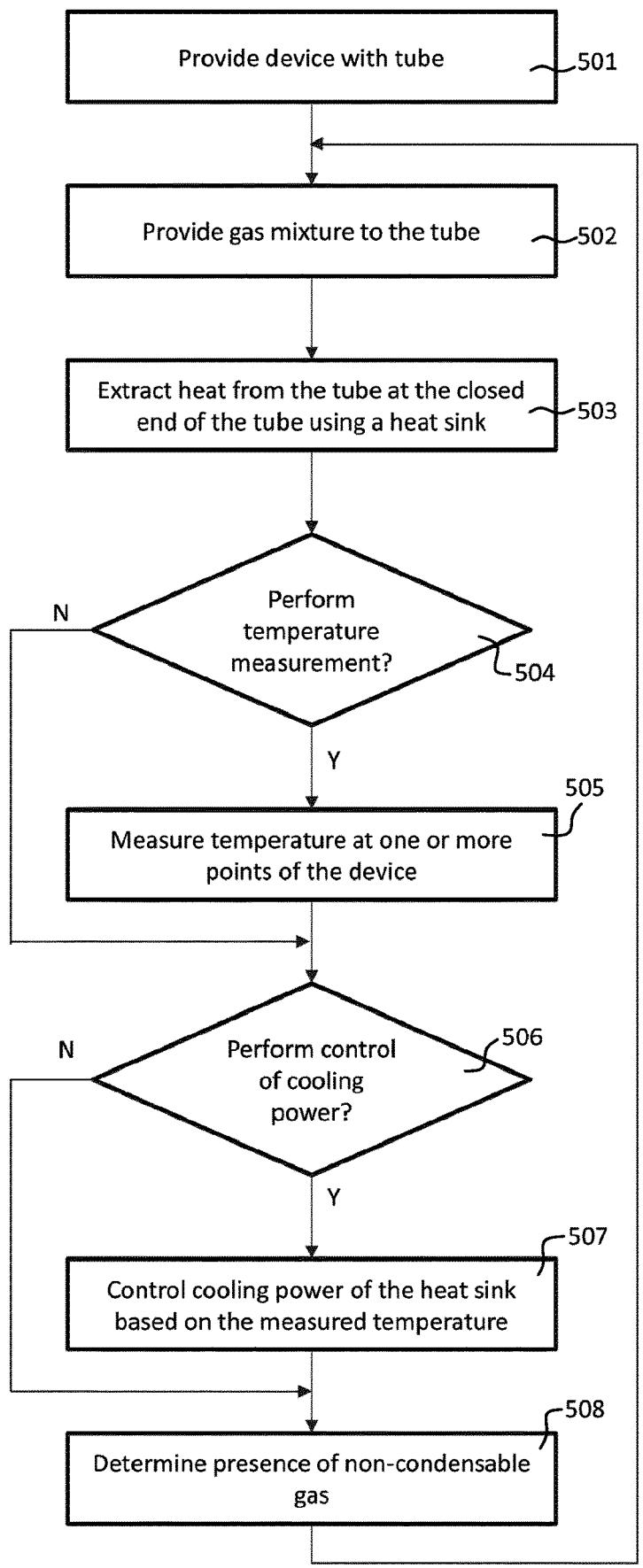
FIG. 5 shows a flowchart illustrating a method of determining a non-condensable gas in a gas mixture.

FIG. 5 illustrates a method of determining a non-condensable gas in a gas mixture. In step 501, a device with a tube having a closed end with a heat sink and an open end is provided, as outlined hereinabove. In step 502, steam or another gas or a gas mixture is provided to the open end of the tube. This step may be part of a steam sterilization procedure, as outlined hereinabove. Sterilization procedures are known in the art per se. As part of step 502 the open end of the tube may be fluidly connected to the sterilizer chamber. In step 503, heat is extracted from the tube at the closed end of the tube using the heat sink. This step may comprise controlling to provide electric power to the heat sink, which may comprise an active component such as a Peltier element. Alternatively, step 503 may comprise pre-cooling a passive cooling element. In step 504, it is decided whether to perform a temperature measurement. In certain implementations the temperature measurement is performed continuously, in other implementations this may be performed at certain time points defined by an application program, for example. In step 505, if the temperature measurement is to be performed, the temperature measurement is performed at one or more points of the device. This step may comprise receiving a signal from the corresponding thermometer or thermometers, converting the signal to a digital value, and storing the digital value in a memory. In step 506, it is decided whether to perform control of the cooling power. This may depend on the implementation (passive or active heat sink). Also, the cooling power may be adjusted at certain time intervals, which may be monitored using a timer in step 506. In step 507, if the cooling power is to be controlled, the cooling power of the heat sink is controlled based on the measured temperature. For example, if the measured temperature at a specific one of the thermometers is below a lower threshold, the cooling power may be reduced. On the other hand, if the measured temperature at the specific thermometer is above an upper threshold, the cooling power may be increased. The specific thermometer may be a thermometer at the heat sink (see 7), at a thermal resistance (see 10a, 10b), or a thermometer on the tube itself (see 8). In the latter case, preferably a thermometer close to the closed end of the tube is used for this purpose. Finally, in step 508, the presence of a non-condensable gas may be detected. For example, the measured temperatures and/or the power supplied to the heat sink is combined and converted to a concentration of non-condensable gas using an equation or a look-up table.

It will be understood that the temperature measurement in step 504/505 and the cooling power control in step 506/507 may be replaced by another method to detect the non-condensable gas. For example, the condensation may be observed visually (e.g., using a transparent tube or a camera), or using a capacitive detection method. Condensation closer to the closed end of the tube indicates a smaller concentration of non-condensable gas.

The present invention has been described above with reference to a number of exemplary embodiments as shown in the drawings. Modifications and alternative implementations of some parts or elements are possible, and are included in the spirit and scope of the present disclosure as defined by the appended claims and their equivalents.

Some or all aspects of the invention may be suitable for being implemented in the form of software, in particular a computer program product. The computer program product may comprise a computer program stored on a non-transitory computer-readable media. Also, the computer program may be represented by a signal, such as an optic signal or an electro-magnetic signal, carried by a transmission medium such as an optic fiber cable or the air. The computer program may partly or entirely have the form of source code, object code, or pseudo code, suitable for being executed by a computer system. For example, the code may be executable by one or more control units, such as controllers or processors. Such controllers and processors, capable of executing a program and controlling a device, are known in the art.

The examples and embodiments described herein serve to illustrate rather than limit the invention. The person skilled in the art will be able to design alternative embodiments without departing from the scope and spirit of the invention, as defined by the appended claims and their equivalents. Reference signs placed in parentheses in the claims shall not be interpreted to limit the scope of the claims. Items described as separate entities in the claims or the description may be implemented as a single hardware or software item combining the features of the items described.

Some examples are disclosed in the following clauses.

1. A device for detecting a gas, comprising
   a tube (1) having an open end (5) and a closed end (12), wherein the tube (1) and the closed end (12) are closed with respect to a fluid (2), and the open end (5) is open to allow the fluid (2) to move into and out of the tube (1); and
   a heat sink (6) configured to extract heat from the tube (1) at the closed end (12) of the tube.
2. The device of clause 1, wherein the heat sink (6) comprises a cooling surface (18) that is fixed facing the tube.
3. The device of clause 2, wherein the cooling surface (18) faces the closed end (12) of the tube.
4. The device according to any preceding clause, wherein the heat sink (6) comprises an active cooling element, for example a Peltier element.
5. The device according to any preceding clause, further comprising at least one thermometer (7, 8, 10) configured to measure a temperature at a specific portion of the device or the fluid (2) inside the tube.
6. The device according to clause 5, further comprising a control unit (430) configured to adjust a cooling power of the heat sink (6) based on a temperature obtained from the thermometer (7).
7. The device according to clause 5 or 6, wherein the control unit (430) is further configured to determine information about a composition of the fluid (2) inside the tube, in particular about a presence of any non-condensable gas in the fluid (2), based on a temperature obtained from the thermometer (7, 8, 10) or a cooling power of the heat sink (6).
8. The device according to clause 5, comprising a plurality of thermometers (8) arranged along the tube (1) in an axial direction (13) of the tube (1), each thermometer of the plurality of thermometers (8) being configured to measure a temperature at a different portion of the tube (1).

9. The device according to clause 8, wherein a distance between adjacent thermometers (8) measured in axial direction (13) along the tube (1) is larger for thermometers that are further away from the closed end (12) of the tube (1) in comparison to thermometers that are closer to the closed end (12) of the tube (1).

10. The device according to any preceding clause, wherein the device is configured to measure a flow of heat between the closed end (12) of the tube and the heat sink (6).

11. The device according to clause 10, comprising a thermal resistor (11) in between the closed end (12) of the tube (1) and the heat sink (6); and a first thermometer (10a) configured to measure a first temperature of the thermal resistor (11) and a second thermometer (10b) configured to measure a second temperature of the thermal resistor (11), wherein the first thermometer (10a) is fixed closer to the heat sink (6) than the second thermometer (10b), and the second thermometer (10b) is fixed closer to the closed end (12) of the tube (1) than the first thermometer (10a).

12. The device according to any preceding clause, further comprising a container (402);

wherein the open end (5) of the tube (1) is fluidly connected to an inside of the container (402) via an opening (408) in a wall (450) of the container (402), and wherein the container (402) is closable to form a substantially closable chamber (401) that is fluidly connected to a lumen of the tube (411, 421).

13. The device according to clause 12, wherein the chamber (401) is a sterilizer chamber.

14. The device according to clause 12 or 13, wherein the container (402) has the opening in a side wall (451) or an upper wall (450) of the container, wherein the chamber (401) is fluidly connected to the inside of the tube (411, 421) via the opening.

15. The device according to clause 14, wherein the tube (411, 421) is fixed to the side wall (451) or upper wall (450) of the container (402) and wherein the tube (411, 421) protrudes from the container (402) in an upward direction.

16. The device according to any preceding clause, wherein a length along a center of the tube (1) from the open end (5) to the closed end (12) is between 10 centimeters and 30 centimeters, or a diameter of the lumen of the tube (1) is between 3 millimeters and 20 millimeters, or a thickness of the wall (15) of the tube (1) is between 1 millimeter and 5 millimeters, or wherein the tube (1) comprises a metal such as Cu, Al, Cr, Fe, or Ni, or any alloy containing any two or more of these elements, or a polymer.

17. A method of detecting a gas, comprising providing (501) steam to a tube having an open end and a closed end, wherein the tube and the closed end are closed with respect to the steam, and the open end is open to allow the steam to move into and out of the tube; and extracting (502) heat from the tube at the closed end of the tube using a heat sink.

REFERENCES

TABLE 1

Patent citations

| Cited patent Filing date Publication date | Applicant | Title |
|---|---|---|
| DE102010016017A1 Mar. 18, 2010 Nov. 24, 2011 | MMM Münchner Medizin Mechanik GmbH | Sterilisator |
| DE202006006926U1 Apr. 29, 2006 Jun. 29, 2006 | Ebro Electronic GmbH & Co. Kg | Device for testing effectiveness of autoclave steam sterilization, e.g. of medical articles, via temperature measurements, including sensors in sterilization zone and removable, easily cleaned measuring chamber |
| EP0841069A2 Nov. 8, 1997 May 13, 1998 | F. & M. Lautenschläger | Verfahren und Vorrichtung zur Analyse von Dampf aus einer Dampfsterilisations oder Dampfdesinfektionsanlage |
| EP1230936A1 | Answers, Solutions and Know-how B.V.i.o | Method and device for determining the process conditions in sterilization |
| U.S. Pat. No. 3,402,991 Aug. 23, 1963 Sep. 24, 1968 | Drayton Castle Ltd. | Sterilizer and control apparatus |
| U.S. Pat. No. 3,479,131 Nov. 4, 1966 Nov. 18, 1969 | Manlove, Alliott & Company Ltd. | Air-detecting device for steam sterilizers |
| U.S. Pat. No. 3,967,494 Feb. 28, 1975 Jul. 6, 1976 | Sybron Corporation | Method and apparatus for detecting entrapped air in a steam sterilizer |
| U.S. Pat. No. 4,115,068 Apr. 6, 1977 Sep. 19, 1978 | Sybron Corporation | Air detecting device for steam or gas sterilizers |
| U.S. Pat. No. 4,594,223 Dec. 20, 1984 Jun. 10, 1986 | American Sterilizer Company | Device for detecting the presence of noncondensable gas in steam sterilizers |
| U.S. Pat. No. 5,270,217 Feb. 1, 1993 Dec. 14, 1993 | Dyke Denis G | Method and article for providing an indication of the presence of air in steam |
| WO201047139 Sep. 18, 2013 Mar. 27, 2014 | 3M Innovation properties | Sterilant challenge device |

TABLE 2

Non-Patent Citations

| Label | Reference |
|---|---|
| [BEN11] | Benoit F, Merger D, Hermsen RJ, and van Doornmalen JPCM. A comparison of four commercially available electronic steam penetration tests according to ISO 11140 part 4. Central Service, 3: 180-184, 2011. |
| [EN 285] | European Committee for Standardization. Standard EN 285: A2: 2009 sterilization - steam sterilizers - large sterilizers, 2015. |
| [EN13060] | European Committee for Standardization. Standard EN 13060, Small Steam Sterilizers. European standard, 2014. |
| [IAWPS] | Wagner W, Cooper JR, Dittmann A, Kijima J, Kretzschmar HJ, Kruse A, Mares R, Oguchi K, Šato H, Stöcker I, Sifiner O, Takaishi Y, Tanishita I, and Trúbenbach IJ. The IAWPS industrial formulation 1997 for the thermodynamic properties of water and steam. Transactions of the ASME, 122: 150-182, 2000. |

TABLE 2-continued

Non-Patent Citations

| Label | Reference |
|---|---|
| [ISO11140-4] | International Organization for Standardization. Standard ISO 11140-4 Sterilization of health care products - Chemical indicators - Part 4: Class 2 indicators as an alternative to the Bowie and Dick-type test for detection of steam penetration. ISO standard, 2007. |
| [ISO17665] | International Organisation for Standardisation. Standard ISO 17665-1. Sterilization of health care products -Moist heat, international organization for standardization, 2006. |
| [MIN66] | Minkowycz WJ and Sparrow EM. Condensation heat transfer in the presence of noncondensables, interfacial resistance, superheating, variable properties, and diffusion. International Journal of Heat and Mass Transfer, 9: 1125-1144, 1966. |
| [MRC59] | Working party on Pressure Steam Sterilizers of the Medical Research Council. Sterilisation by steam under increased pressure. The Lancet, 273: 425-435, 1959. |
| [ROS69] | Rose JW. Condensation of a vapour in the presence of a non-condensing gas. International Journal of Heat and Mass Transfer, 12: 233-237, 1969. |
| [SYK67] | Sykes G. Disinfection & sterilization. 2nd edition with corrections. E & FN Spon Ltd, London, 1967. |
| [VDO12-2] | van Doornmalen JPCM, Hermsen RJ, and Kopinga K. Six commercially available class 6 chemical indicators tested against their stated values. Central Service, 6: 400-404, 2012. |
| [VDO13-2] | van Doornmalen JPCM, Rietmeijer AGM, Feilzer AJ, and Kopinga K. Monitoring of steam sterilization processes in the dental office. Central Service, 6: 435-438, 2013. |
| [VDO13-3] | van Doornmalen JPCM and Kopinga K. Measuring non-condensable gases in steam. Review of Scientific Instruments, 84: 115106, 2013. |
| [VDO14-1] | van Doornmalen JPCM, Tessarolo F, and Kopinga K. Measurements of only pressure and temperature are insufficient to monitor steam sterilization processes: a case study. Central Service, 4: 250-253, 2014. |
| [VDO16-3] | van Doornmalen JPCM Riethoff W. A case study of steam penetration monitoring indicates the necessity of Every Load Monitoring of steam sterilization processes, Central Service 5: 320-324, 2016. |

The invention claimed is:

1. A device for detecting a gas, comprising
a tube having an open end and a closed end, wherein the tube and the closed end are closed with respect to a fluid, and the open end is open to allow the fluid to move freely into and out of the tube, wherein the tube is configured to allow a condensed portion of the fluid to be removed from the tube by gravitation;
a heat sink configured to extract heat from the tube at the closed end of the tube to keep the closed end of the tube at a constant target temperature;
a thermal resistor in between the closed end of the tube and the heat sink;
a first thermometer configured to measure a first temperature of the thermal resistor;
a second thermometer configured to measure a second temperature of the thermal resistor, wherein the first thermometer is fixed closer to the heat sink than the second thermometer, and the second thermometer is fixed closer to the closed end of the tube than the first thermometer;
a control unit configured to determine information about a composition of the fluid inside the tube based on a temperature obtained from the first thermometer and a temperature obtained from the second thermometer while the closed end of the tube is kept at the constant target temperature or based on a cooling power of the heat sink determined while the closed end of the tube is kept at the constant target temperature, wherein the information includes whether or not there is a presence of any non condensable gas in the fluid.

2. The device of claim 1, wherein the heat sink comprises a cooling surface that is fixed facing the tube.

3. The device of claim 2, wherein the cooling surface faces the closed end of the tube.

4. The device according to claim 1, wherein the heat sink comprises an active cooling element.

5. The device according to claim 4, wherein the active cooling element is a Peltier element.

6. The device according to claim 1, wherein the control unit is further configured to adjust a cooling power of the heat sink based on a temperature obtained from the thermometer.

7. The device according to claim 1, comprising a plurality of thermometers arranged along the tube in an axial direction of the tube, each thermometer of the plurality of thermometers being configured to measure a temperature at a different portion of the tube.

8. The device according to claim 7, wherein a distance between adjacent thermometers measured in axial direction along the tube is larger for thermometers that are further away from the closed end of the tube in comparison to thermometers that are closer to the closed end of the tube.

9. The device according to claim 1, wherein the device is configured to measure a flow of heat between the closed end of the tube and the heat sink.

10. The device according to claim 1, further comprising a container;
wherein the open end of the tube is fluidly connected to an inside of the container via an opening in a wall of the container, and wherein the container is closable to form a substantially closable chamber that is fluidly connected to a lumen of the tube.

11. The device according to claim 10, wherein the chamber is a sterilizer chamber.

12. The device according to claim 10, wherein the container has the opening in a side wall or an upper wall of the container, wherein the chamber is fluidly connected to the inside of the tube via the opening.

13. The device according to claim 12, wherein the tube is fixed to the side wall or upper wall of the container and wherein the tube protrudes from the container in an upward direction.

14. The device according to claim 1, wherein a length along a center of the tube from the open end to the closed end is between 10 centimeters and 30 centimeters, or a diameter of the lumen of the tube is between 3 millimeters and 20 millimeters, or a thickness of the wall of the tube is between 1 millimeter and 5 millimeters, or wherein the tube comprises a metal such as Cu, Al, Cr, Fe, or Ni, or any alloy containing any two or more of these elements, or a polymer.

15. A device for detecting a gas, comprising
a tube having an open end and a closed end, wherein the tube and the closed end are closed with respect to a fluid, and the open end is open to allow the fluid to move freely into and out of the tube, wherein the tube is configured to allow a condensed portion of the fluid to be removed from the tube by gravitation;

a heat sink configured to extract heat from the tube at the closed end of the tube to keep the closed end of the tube at a constant target temperature, wherein the heat sink at the closed end of the tube is the only heat sink along the tube or the device is configured so that during detection of a non-condensable gas no further active heat sinks are activated except for the heat sink at the closed end of the tube;

at least one thermometer configured to measure a temperature at a specific portion of the device or a temperature of the fluid inside the tube; and a control unit configured to determine information about a composition of the fluid inside the tube based on a temperature obtained from the thermometer while the closed end of the tube is kept at the constant target temperature or based on a cooling power of the heat sink determined while the closed end of the tube is kept at the constant target temperature, wherein the information includes whether or not there is a presence of any non-condensable gas in the fluid.

16. A method of detecting a gas, comprising providing steam to a tube having an open end and a closed end, wherein the tube and the closed end are closed with respect to the steam, and the open end is open to allow the steam to move into and out of the tube, wherein a condensed portion of the fluid is allowed to be removed from the tube by gravitation; and extracting heat from the tube at the closed end of the tube using a heat sink to keep the closed end of the tube at a constant target temperature, wherein a thermal resistor is provided in between the closed end of the tube and the heat sink;

measuring, by a first thermometer, a first temperature of the thermal resistor;

measuring, by a second thermometer, a second temperature of the thermal resistor, wherein the first thermometer is fixed closer to the heat sink than the second thermometer, and the second thermometer is fixed closer to the closed end of the tube than the first thermometer; and determining information about a composition of the fluid inside the tube, based on a temperature obtained from the first thermometer and the second thermometer while the closed end of the tube is kept at the constant target temperature or based on a cooling power of the heat sink determined while the closed end of the tube is kept at the constant target temperature, wherein the information includes whether or not there is a presence of any non condensable gas in the fluid.

17. A method of detecting a gas, comprising providing steam to a tube having an open end and a closed end, wherein the tube and the closed end are closed with respect to the steam, and the open end is open to allow the steam to move into and out of the tube, wherein a condensed portion of the fluid is allowed to be removed from the tube by gravitation;

extracting heat from the tube at the closed end of the tube using a heat sink to keep the closed end of the tube at a constant target temperature, wherein the heat sink at the closed end of the tube is the only heat sink along the tube or wherein, during detection of a non-condensable gas, no further active heat sinks are activated except for the heat sink at the closed end of the tube;

measuring a temperature using at least one thermometer configured to measure the temperature at a specific portion of the device or a temperature of the fluid inside the tube; and determining information about a composition of the fluid inside the tube, based on a temperature obtained from the thermometer while the closed end of the tube is kept at the constant target temperature or based on a cooling power of the heat sink determined while the closed end of the tube is kept at the constant target temperature, wherein the information includes whether or not there is a presence of any non-condensable gas in the fluid.

* * * * *